United States Patent [19]

De Bruin et al.

[11] Patent Number: 5,216,487
[45] Date of Patent: Jun. 1, 1993

[54] TRANSMISSIVE SYSTEM FOR CHARACTERIZING MATERIALS CONTAINING PHOTOREACTIVE CONSTITUENTS

[75] Inventors: David C. De Bruin, San Jose, Calif.; Martin R. Hannifan, Salem, Oreg.

[73] Assignee: Site Services, Inc., Santa Clara, Calif.

[21] Appl. No.: 704,091

[22] Filed: May 22, 1991

[51] Int. Cl.$^5$ ............................................. G01N 21/00
[52] U.S. Cl. ...................................... 356/432; 356/443
[58] Field of Search ................. 356/432, 445, 443, 51, 356/244; 250/372; 430/30

[56] References Cited

U.S. PATENT DOCUMENTS

| | | | |
|---|---|---|---|
| 3,669,554 | 6/1972 | Horer et al. | 356/244 |
| 3,708,229 | 1/1973 | Pircher | 356/108 |
| 4,129,781 | 12/1978 | Doyle | 250/341 |
| 4,145,142 | 3/1979 | Mikeman | 356/229 |
| 4,198,261 | 4/1980 | Busta et al. | 156/626 |
| 4,312,732 | 1/1982 | Degenkolb et al. | 204/192 |
| 4,377,436 | 3/1983 | Donnelly et al. | 156/626 |
| 4,454,001 | 6/1984 | Sternheim et al. | 156/626 |
| 4,469,424 | 9/1984 | Matsui et al. | 354/298 |
| 4,474,864 | 10/1984 | Chow et al. | 356/51 |
| 4,488,810 | 12/1984 | Hatanaka et al. | 356/244 |
| 4,611,919 | 9/1986 | Brooks, Jr. et al. | 356/357 |
| 4,647,172 | 3/1987 | Batchelder et al. | 354/298 |
| 4,668,860 | 5/1987 | Anthon | 250/225 |
| 4,851,311 | 7/1989 | Millis et al. | 430/30 |
| 4,874,240 | 10/1989 | Watts et al. | 356/73 |
| 4,876,453 | 10/1989 | Wirick | 250/332 |
| 4,972,072 | 11/1990 | Hauser et al. | 250/225 |

OTHER PUBLICATIONS

Integrated Circuit Metrology, Inspection, and Process Control III, Society of Phot-Optical Instrumentation Engineers, Proceedings of SPIE-The International Society for Optical Engineering, vol. 1087 Feb., 1989.
The Use of Develop End Point Detection to Eliminate Photolithographic Process Variation, Nygren, C. et al.
Lithographic Optimization Using Photoresist Contrast, Mack, Chris Proceeding of KTI Microlithography Seminar, Nov., 1990 San Diego.

Primary Examiner—Richard A. Rosenberger
Attorney, Agent, or Firm—Burns, Doane, Swecker and Mathis

[57] ABSTRACT

A transmissive system for characterizing the photochemical reactivity and solubility properties of materials, such as photoresist, that contain one or more photoactive constituents and that can be formed as films on optically-transparent substrates. The system operates to detect the intensity of light transmitted through the photo-active material and the optically-transparent substrate. Generally speaking, the system comprises: a) an optically-transparent substrate means for providing a substrate for a film formed of a material that contains one or more photo-active constituents; b) exposure means for transmitting at least one selected wavelength of light through at least one selected area of the film; and c) detection means for detecting the intensity of light transmitted through the film and optically-transparent substrate means.

21 Claims, 2 Drawing Sheets

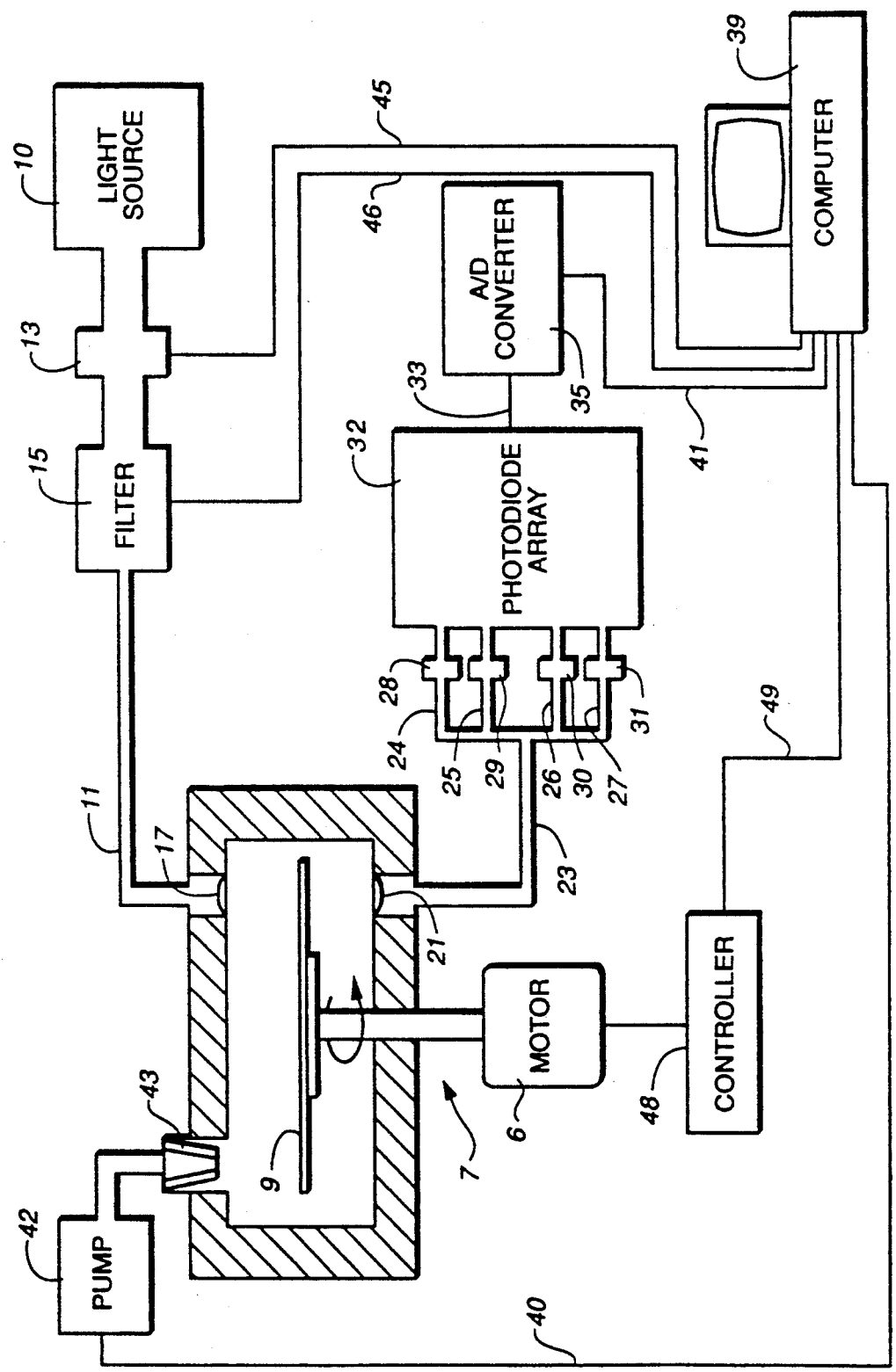
FIG._1

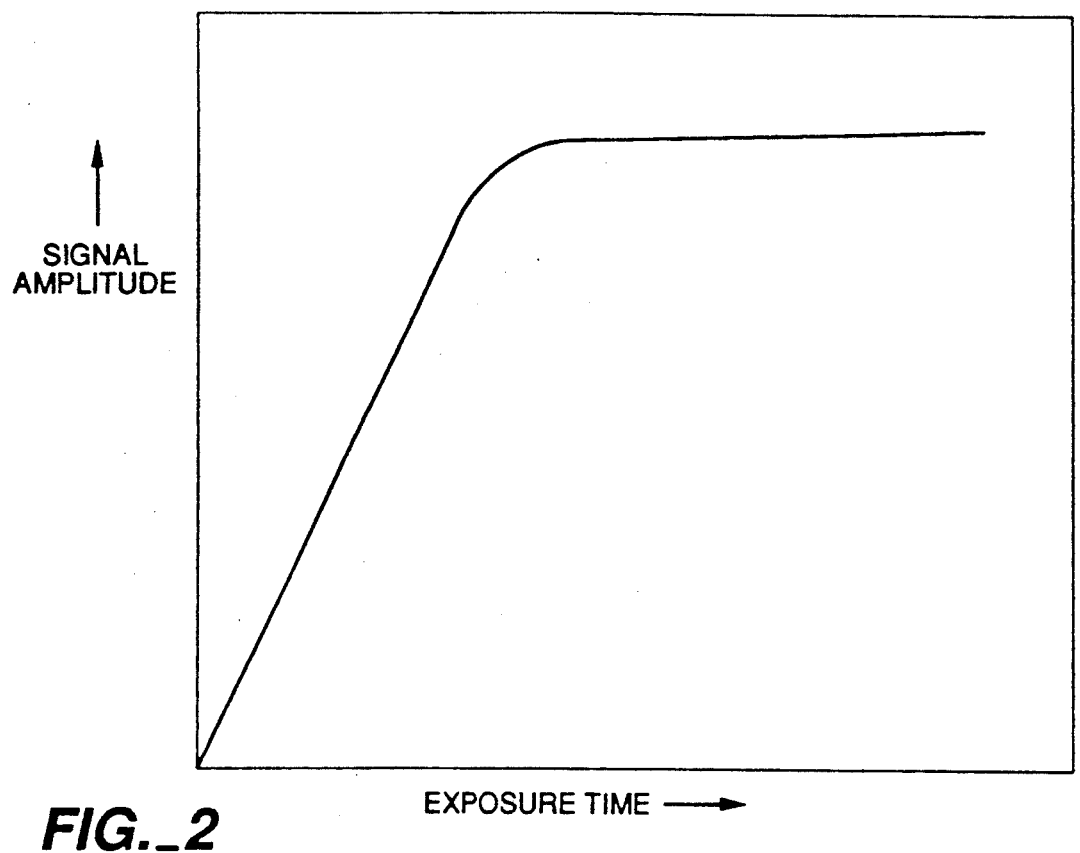
FIG._2
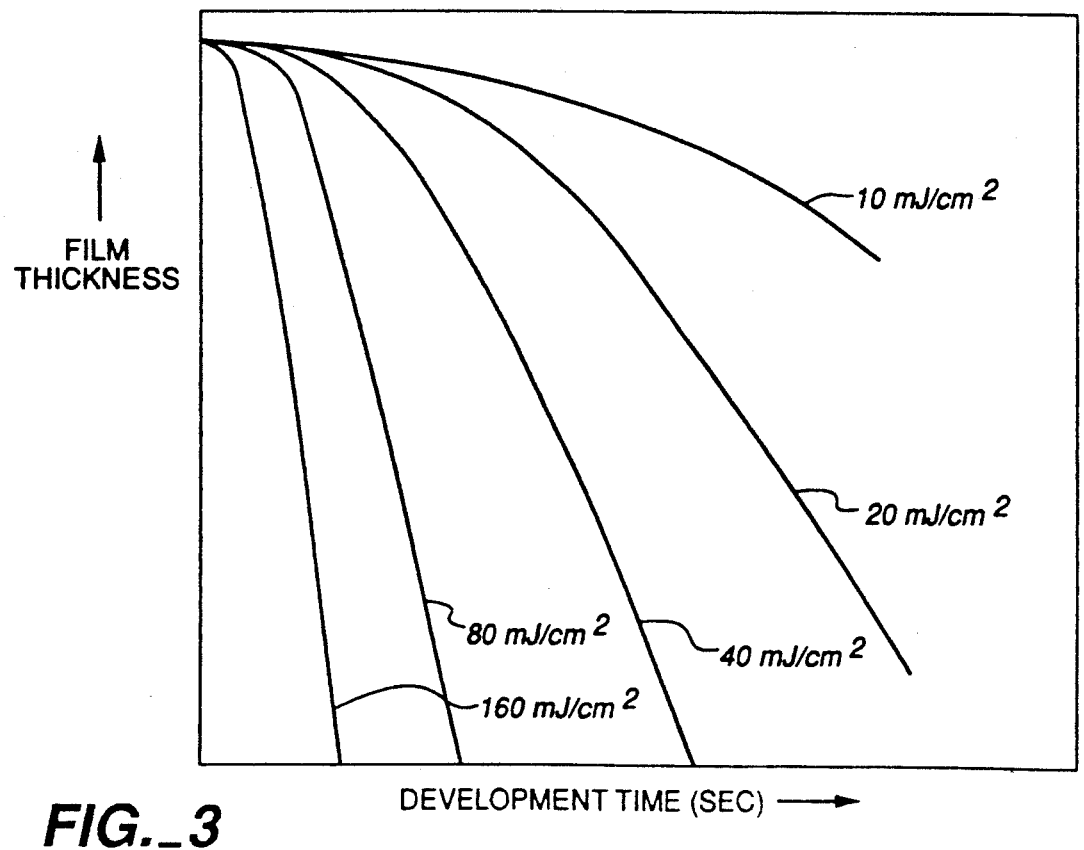
FIG._3

TRANSMISSIVE SYSTEM FOR CHARACTERIZING MATERIALS CONTAINING PHOTOREACTIVE CONSTITUENTS

BACKGROUND OF THE INVENTION

Field of the Invention

The present invention relates to systems for characterizing the photochemical reactivity and solubility properties of materials, such as photoresist, that contain one or more photo-active constituents.

State of the Art

As used in lithography processes for the fabrication of semiconductor integrated circuits, photoresist materials normally consist of three components: a resin component, a photo-active component (PAC), and a solvent component. In photoresist materials of the so-called positive-working type, the resin component is typically an alkaline-soluble phenolic polymer. The PAC component is an alkaline-insoluble material, typically a diazoquinone moiety. The solvent component provides a medium in which the resin and PAC constituents are soluble; in normal practice, the solvent component is evaporated after the photoresist material is dispensed onto a substrate.

PAC materials, when exposed to actinic wavelengths of light, undergo chemical "photo-bleaching" reactions. When the absorption of actinic wavelengths no longer changes during an exposure process, a photoactive material is said to be one-hundred percent photo-bleached, or fully exposed. Prior to photo-bleaching PAC materials inhibit solubility in alkaline solutions—usually referred to as "developer" solutions. As a result of photo-bleaching, however, positive-working PAC materials produce a reaction product that is soluble in aqueous alkaline solutions. Therefore, actinic exposure increases the solubility of positive-working photoresist materials in developer solutions.

In photoresist materials of the negative-working type, the PAC and resin components are soluble in alkaline developer solutions until those materials are exposed to actinic light. After exposure, the negative-working PAC components become insoluble.

It is well known to use ultraviolet (UV) spectrophotometer systems for measuring the absorption characteristics of PAC-containing materials. The UV spectrophotometer systems operate to measure the difference in intensity of UV light transmitted through two parallel optical paths: one having no PAC-containing material, and one including PAC-containing material. Those spectrophotometric measurements can be compared and then related to the absorption properties and thickness of PAC-containing materials.

It is also known to use spectrophotometric measurements over a single optical path during actinic exposure processes for determining the photo-bleaching properties of PAC-containing materials. More particularly, the photo-bleach characteristics of the PAC-containing materials can be modelled based upon measurements of the changes in intensity of the transmitted light as a function of the actinic exposure time. Such measurements, also can be used for determining the concentration of PAC constituents in the optical path.

Photo-bleach curves provide a basis for calculating characteristic parameters—often referred to as A, B, and C parameters. The "A" parameter relates to the difference in transmittance between fully exposed and the unexposed PAC material. The "B" parameter relates to the transmittance of fully exposed PAC material. The "C" parameter relates to the rate of change of transmittance of PAC materials during exposure processes and relative differences in transmittance between fully exposed and un-exposed materials.

Interferometric techniques are typically used for measuring the solubility characteristics of unexposed, partially exposed, and fully exposed PAC-containing materials. In operation, interferometric systems detect interference patterns of coherent light reflected from a film of a PAC-containing material that has been formed on a substrate. The interference patterns arise because of phase differences between light reflected from the surface of the PAC-containing film and light reflected from the interface surface between the PAC-containing material and the carrier substrate. During "development" processes when exposed areas of PAC-containing material are being removed from a substrate, the interference patterns can be related to changes in the PAC-containing material thickness. Also, the interferometric data can be presented as "development rate curves" that depict the change in material thickness with the duration of a development process.

SUMMARY OF THE INVENTION

The present invention provides a transmissive system for characterizing the photochemical reactivity and solubility properties of materials, such as photoresist, that contain one or more photo-active constituents and that can be formed as films on optically-transparent substrates. More particularly, the systems detect the intensity of light transmitted through the material and the optically-transparent substrate during (or, before and after) actinic exposure processes and during (or, before and after) material removal (development) processes.

In practice, systems according to the present invention can be used for determining various conditions—such as exposure energy, and development process time—that are required for uniform fabrication processes for the production of semiconductor integrated circuits. Also, the transmissive-based system of the present invention can be used for both process and material characterization experimentation. Such experiments include, for instance, the determination of photo-bleaching characteristics of PAC-containing materials; the solubility the unexposed, partially exposed, and fully exposed PAC-containing material; the solubility characteristics of such materials: and the effects of material processing conditions upon photo-bleaching and solubility characteristics of PAC-containing materials.

Generally speaking, a transmissive-based system according to the present invention comprises: a) an optically-transparent substrate means for providing a substrate for a film formed of a material that contains one or more photo-active constituents; b) exposure means for transmitting at least one selected wavelength of light through at least one selected area of the film; and c) detection means for detecting the intensity of light transmitted through the film and optically-transparent substrate means. In the preferred embodiment, a system according to the present invention includes a rotation means for controllably rotating the optically-transparent substrate means in a plane perpendicular to the incident light provided by the exposure means. Preferably, the rotation means comprises an angular stepping motor, a holder for the optically-transparent substrate means, and a position control means for controlling the angular stepping motor.

BRIEF DESCRIPTION OF THE DRAWINGS

The present invention can be further understood by referring to the following description and the appended drawings. In the drawings, like elements are provided with the same reference numerals.

FIG. 1 is a schematic block diagram of a system for the measurement of light transmission characteristics of PAC-containing-material film;

FIG. 2 shows an example of a photo-bleach curve provided by the system of FIG. 1 for the characterization of the PAC-containing-material film; and FIG. 3 shows an example of a development rate curve provided by the system of FIG. 1 for the characterization of the PAC-containing-material film.

DETAILED DESCRIPTION OF THE PREFERRED EMBODIMENTS

As shown in FIG. 1, a transmissive system for characterizing photo-active films includes a rotatable holder assembly 7 that holds a disk-like substrate 9. (In the following the disk-like substrate is referred to herein as a "wafer.") The rotatable holder assembly also includes a motor 6 that drives the wafer to rotate about its central axis. The wafers that are used in the transmissive system are made of an optically transparent materials—normally quartz or glass—that are suitable substrates for thin films comprised of photo-active materials.

The transmissive system of FIG. 1 also includes a light source 10 for providing light to the receiving end of a fiber optic cable 11. The system also includes a shutter device 13 which is mounted in the light path from source 10 for selectively blocking light from passing into the receiving end of the cable 11. Further, an optical filter bank 15 is mounted for filtering the spectral content of the light that enters the fiber optic cable 11 from the source 10. In practice, the light source is a high intensity lamp with an emission range that includes UV wavelengths. Also, a collimating lens 17 is mounted adjacent the light-emitting end of fiber optic cable 11 for uniformly distributing the emitted light across a selected area on the surface of a wafer 9. Thus, in the following, the phrase "illumination path" is used for designating the combination of the light source 10, the shutter device 13, the filter bank 15, the fiber-optic cable 11, and the collimating lens 17.

Further, the system of FIG. 1 includes a condensing lens 21 which is mounted below wafer 9 in the path of the incident light for collecting light that passes through the wafer. A multi-furcated fiber optic cable 23 is connected to condensing lens 21 for providing multiple independent optical channels—designated by numbers 24, 25, 26 and 27—each of which connects to an optical spectral filter as designated by numbers 28, 29, 30, and 31, respectively. All four of the optical filters are coupled to a photodiode array 32.

In operation of the system of FIG. 1, the output signals from the photodiode array 32 are analog voltage signals. The amplitudes of those signals are proportional to the intensity of light received by the photodiodes in the array 32. These analog voltage signals are carried to a conventional analog-to-digital converter 35 where they are amplified and converted to digital values.

As further shown in FIG. 1, a computer 39 receives the digital signals via a serial interface 41. In practice, computer 39 is a conventional microprocessor-based computer that, as will be explained below, operates upon the digitized signals for computing characteristic parameters of PAC-containing materials. As indicated in the drawing, the computer 39 also is used for controlling a number of components in the system. Specifically, computer 39 controls the shutter device 13 (via a serial interface 45), the optical filter bank 15 (via a serial interface 46), and a motor controller 48 for motor 6 (via a serial interface 49).

Further as shown in FIG. 1, a dispenser system for dispensing developer solution can be mounted for spraying developer solution onto wafers held by the rotatable holder assembly 7. Preferably, the dispensing system also operates to dispense rinse solution for rinsing the residual developer solution and contaminants from exposed surfaces of the wafer after development. In the illustrated embodiment, the dispensing system includes a solution pump 42 and nozzle assembly 43. The computer 39, via a serial interface 44, controls the dispensing system.

As shown in FIG. 2, the photochemical-reactivity of a photoresist film can be characterized by a photo-bleach curve that depicts the intensity of actinic light transmitted through the photoresist film and its optically-transparent substrate (i.e., a wafer 9) as a function of exposure time. The illustrated photo-bleach curve indicates, as is typical, that the transmission of actinic wavelengths increase with the exposure period, i.e., with increasing photochemical conversion of the PAC constituents to their reaction products. The exact shape of a particular photo-bleach curve depends upon the composition of the particular PAC material, upon the composition and interactions of non-photo-active constituents in the PA material, and upon process conditions.

Further with regard to FIG. 2, it is well known that the concentration of PAC constituents in a film undergoing photo-bleaching is proportional to the logarithm of the transmission intensity recorded in a photo-bleach curve for the film.

In operation of the system of FIG. 1, a thin film that includes a photo-active constituent is formed on optically-transparent wafer 9. Then, the coated wafer is placed in holder assembly 7 and actinic light is directed onto the wafer via lens 17. The light is transmitted through the wafer, collected by lens 21, and detected by the photodiode array 32. The detected values are operated upon by A/D convertor 35 and computer 39 to produce photo-bleach curves. In practice, the collection of data is terminated when the slope of the photo-bleach curve approaches zero, indicating that bleaching has gone to completion.

A photo-bleach curve that has been obtained by use of the transmissive system of FIG. 1 can be used for computing characteristic exposure parameters such as the "A", "B", and "C" parameters for photoresist materials. When the system is used for this purpose, a photoresist film is applied to a wafer 9, and the wafer is held stationary by the holder assembly 7 while the shutter device 13 is actuated to expose a small area of the photoresist film. During the exposure process, the array of photodiodes are sampled at a high rate (e.g., twenty to forty samples per second). The sample data—representing the intensity of light transmitted through the photoresist film as a function of time—is used for constructing photo-bleach curves, from which the "A", "B", and "C" parameters can be derived in a known manner.

The system of FIG. 1 can also be used in procedures that are sometimes referred to as "contrast curve" experiments for determining development rate parameters. The development rate parameters can compromise, for example, R1, R2, R3, and "contrast." The R1, R2, and R3 parameters relate to discrete photoresist development rates for 0%, 50%, and 100% photo-bleach compositions, respectively. The contrast parameter, often referred to as the "gamma" parameter, relates to the rate of change of the development rate with respect to the logarithm of the exposure energy.

To conduct a contrast curve experiment with the system of FIG. 1, the stepper motor 6 is operated to rotate the wafer 9 during the exposure process. Normally, the rotation speed is sufficiently slow that exposure of the photoresist film progressively decreases from 100% photo-bleach to 0% photo-bleach along the perimeter of the wafer (within one rotation). During the exposure process, computer 39 collects and stores information on the intensity of the transmitted light, the angular position of the wafer, and the exposure time. After exposure process, an actinic wavelength is selected which has been selectively absorbed by the non-photo-active constituents of the film. (Filter assembly 15 is employed for selecting a particular wavelength.) Then, the exposed wafer is rotated and the intensity of the transmitted light at the selected wavelength is recorded as a function of the angular position of the wafer.

After completion of a pre-develop data collection phase, a photoresist film and its substrate wafer can be removed from the system of FIG. 1 and can be developed using appropriate developer solutions and equipment. Alternatively, development can be done with the system of FIG. 1. In that case, the stepper motor 6 is operated to rotate a wafer (carrying an exposed film including a PAC) while the developer dispensing system operates to initiate development of the photoresist film. The intensity of light transmitted through the photoresist film and the wafer is monitored during the development process. Based upon the monitored values, changes in the photoresist film thickness with development time and the exposure energies can be calculated as shown by way of example in FIG. 3.

Also, the light transmission can be continuously monitored for a selected period as the development process proceeds or until the transmission intensity of the maximum exposure area ceases to change, thus, indicating development completion. This data can be compared to pre-develop data, thereby enabling determination of dynamic changes of development rate of the film relative to the exposure energy associated with each locale. Also, the final light transmission intensities can be compared to the pre-develop values to determine the "static" film thickness change after development.

By monitoring the wavelengths that are specific to absorption frequencies of the PAC constituent during the exposure process and by monitoring the wavelengths specific to the non-photo-active constituents during the development process, data can be collected for determining chemical and functional characteristics of the PAC-containing material as described in the following.

During system initialization, a user can specify measurement and equipment control parameters such as:

Exposure wavelength;
Stepper motor angular stepping distance, rotational velocity and rotation acceleration rate during exposure, pre-develop, develop, and post-develop phases;
Development time;
Exposure time gradients;
Photo-bleach curve minimum slope at exposure process completion;
Development process monitored wavelength(s);
Photodiode gain; and
Data sampling rates.

Prior to exposure of a photo-active film, readings from the analog-to-digital convertor are calibrated by measuring the intensity of the incident light at the substrate plane using a calibrated, external radiometer. For example, intensities are measured using the system of FIG. 1, and then the same intensities are measured at the substrate plane using a calibrated, external radiometer. The radiometer values are entered in computer 39 to enable a linear regression correlation with the measurement values.

Further in operation of the system of FIG. 1, during exposure of a photo-active film, a real-time graph of transmitted light intensity versus time can be displayed for selected wavelengths. Selection of wavelengths is accomplished by employing the optical filters 28-31. Then, at the time of initiation of the exposure process, the stepper motor 6 rotates the wafer 9 at the selected acceleration rate while the shutter device(s) 13 are actuated to pass the selected light wavelength(s) to the photo-active film. The detected transmission intensity values are displayed as the wafer is rotated. After the exposure process is complete, the intensity values are stored for later analysis.

Alternatively, the system of FIG. 1 can be used where there are discrete exposure areas on a wafer. In this case, the stepper motor 6 rotates a wafer 9 to a first selected angular position and stops. Then, the shutter device 13 is actuated to allow light at the selected wavelength(s) to be transmitted through the photo-film. When the intensity of the transmitted light attains a pre-determined level, the shutter device 13 is closed, and the stepper motor 6 rotates the wafer a second pre-determined angular position. Then, the shutter device is again actuated. This process repeats until the wafer is rotated through one complete turn (i.e. 360°). For each location at which rotation is stopped, a unique exposure time is employed. Again, the intensity data for each exposed area can be displayed in real time.

Further, the system of FIG. 1 can be used, prior to development of exposed photo-active films, to make measurements of transmitted light intensities at a wavelength specific to an absorption frequency of the non-photo-active constituents of the film. In this case, the optical filter bank 15 is activated and one of its bandpass filter is selected that passes light which is selectively absorbed by the non-photo-active constituents of the film. Then, the stepper motor 6 rotates the wafer 9 to the 0° position, and the shutter device 13 is activated to transmit light (at the selected wavelength) to the film, wafer and detector systems. Thereafter data collection is accomplished as described above.

Upon completion of data collection for exposure and development processes, a user of the system of FIG. 1 can select several data analysis options for computing characteristic parameters for the PAC-containing material. For example, the transmission intensity can be analyzed versus exposure time or energy; or the normalized PAC concentration can be analyzed versus exposure time or energy.

Examples of analysis options for a development process include:
- transmission intensity versus development time;
- film thickness versus development time;
- development rate versus development time; and
- development rate versus film thickness.

Examples of analysis options for a combined exposure and development processes include:
- PAC concentration versus exposure time or energy;
- film thickness versus PAC concentration;
- film thickness versus exposure time or energy;
- development rate versus exposure time or energy;
- development rate versus PAC concentration;
- contrast versus exposure time or energy;
- contrast versus PAC concentration; and
- contrast versus development time.

In practice, the above-listed analyses options are used with data point regression analyses to quantify characteristic parameters. The quantified parameters can be used for selecting processing conditions, exposure energy and development times that are appropriate for particular photo-active materials. Also, measurement data and computed characteristic parameters can be used for determining material formulation processes in photo-active film formulation practices.

It will be appreciated that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description, and all the changes that come within the meaning and range and equivalents thereof, are intended to be embraced therein.

What is claimed is:

1. A transmissive-based system for characterizing the photochemical reactivity and solubility properties of materials containing one or more photo-active constituents, comprising:
   optically-transparent substrate means for providing a substrate for a film formed of a material that contains one or more photo-active constituents and one or more non-photo-active constituents;
   selection means for selecting a band of wavelengths of light to be transmitted, from among a plurality of such bands available for selection, one band including only actinic wavelengths of light and another band including only wavelengths of light specific to absorption frequencies of said one or more non-photo-active constituents;
   exposure means for transmitting a selected band of light through at least one area of the film;
   detection means for detecting the intensity of light transmitted through the film and optically-transparent substrate means;
   development means for developing said film; and
   means for using intensities of transmitted acinic wavelengths of light and transmitted wavelengths of light specific to absorption frequencies of said one or more non-photo-active constituents to characterize the exposure and solubility characteristics of said materials.

2. A system according to claim 1 including rotation means for controllably rotating the optically-transparent substrate means in a plane perpendicular to the incident light provided by the exposure means.

3. A system according to claim 1 wherein the rotation means comprises an angular stepping motor, a holder for the optically-transparent substrate means, and a position control means for controlling the angular stepping motor.

4. A system according to claim 1 including first dispensing means for dispensing developer solution onto the film and the optically-transparent substrate means.

5. A system according to claim 4 including second dispensing means for dispensing a rinsing solution onto the film and the optically-transparent substrate means.

6. A system according to claim 4 wherein the first dispensing means comprises at least one liquid pump and dispensing nozzle.

7. A system according to claim 1 wherein the optically transparent substrate means comprises at least one of quartz and glass.

8. A system according to claim 7 wherein the detection means further includes means for determining exposure time, exposure wavelengths, exposure intensity, and thickness changes of the photosensitive film during a development process.

9. A system according to claim 1 wherein the detection means detects the intensity of transmitted light as a function of at least one of the energy of the exposing light, the wavelength of the exposing light, and the exposure duration.

10. A system according to claim 9 wherein the detection means includes:
    analog-to-digital conversion means for converting the detected values to digital values; and
    storage means for storing the digital values.

11. A transmissive system for characterizing the photochemical reactivity and solubility properties of materials containing one or more photo-active constituents, comprising:
    optically-transparent substrate means for providing a substrate for a film formed of a material that contains one or more photo-active constituents and one or more non-photo-active constituents;
    selection means for selecting a band of wavelengths of light to be transmitted, from among a plurality of such bands available for selection, one band including only actinic wavelengths of light and another band including only wavelengths of light specific to absorption frequencies of said one or more non-photo-active constituents;
    exposure means for transmitting a selected band of light through at least one area of the film;
    rotation means for controllably rotating the optically-transparent substrate means in a plane perpendicular to the incident light provided by the exposure means;
    detection means for detecting the intensity of light transmitted through the film and optically-transparent substrate means;
    development means for developing said film; and
    means for using intensities of transmitted acinic wavelengths of light and transmitted wavelengths of light specific to absorption frequencies of said one or more non-photo-active constituents to characterize the exposure and solubility characteristics of said materials.

12. A system according to claim 11 wherein the rotation means comprises an angular stepping motor, a holder means for the optically-transparent substrate means, and a position control means for controlling the angular stepping motor.

13. A system according to claim 11 including first dispensing means for dispensing developer solution onto the film and the optically-transparent substrate means.

14. A system according to claim 13 including second dispensing means for dispensing a rinsing solution onto the film and the optically-transparent substrate means.

15. A system according to claim 11 wherein the optically-transparent substrate means comprises at least one of quartz or glass.

16. A system according to claim 11 wherein the detection means detects the intensity of transmitted light as a function of at least one of the energy of the exposing light, the wavelength of the exposing light, and the exposure duration.

17. A system according to claim 16 wherein the detection means further includes means for determining thickness changes of the film during a development process.

18. A system according to claim 16 wherein the detection means includes:

analog-to-digital conversion means for converting the detected values to digital values.

19. A transmissive process for characterizing the exposure and solubility characteristics of materials that contain one or more photo-active constituents, comprising the steps of:

on an optically-transparent substrate, forming a film of a material that contains one or more photo-active constituents and one or more non-photo-active constituents;

exposing at lest one selected area of the film by transmitting selected actinic wavelengths of light through the film and the optically-transparent substrate means;

detecting the intensity of the transmitted actinic light;

developing at least one of the exposed areas of the film;

transmitting selected wavelengths of light specific to absorption frequencies of said one or more non-photo-active constituents through said at least one of the exposed areas of the film and through the optically-transparent substrate means;

detecting the intensity of the transmitted light specific to absorption frequencies of said one or more non-photo-active constituents; and using intensities of the transmittal actinic light and the transmitted light specific to absorption frequencies of said one or more non-photo-active constituents to characterize the exposure and solubility characteristics of said materials.

20. A process according to claim 19 further including the steps of:

rinsing the developed film and substrate means by dispensing rinse solution to the surfaces of the film and substrate means.

21. A process according to claim 19 wherein the exposure step further comprises exposing at different selected areas of the film to predetermined different intensities of actinic wavelengths of light.

* * * * *